(12) United States Patent
Blankenship et al.

(10) Patent No.: US 7,521,393 B2
(45) Date of Patent: Apr. 21, 2009

(54) SELECTIVE HYDROGENATION CATALYST DESIGNED FOR RAW GAS FEED STREAMS

(75) Inventors: Steven A. Blankenship, Radcliff, KY (US); Jennifer A. Boyer, Jeffersonville, IN (US); Gary R. Gildert, Houston, TX (US)

(73) Assignee: Süd-Chemie Inc, Louisville, KY (US)

( * ) Notice: Subject to any disclaimer, the term of this patent is extended or adjusted under 35 U.S.C. 154(b) by 868 days.

(21) Appl. No.: 10/900,446

(22) Filed: Jul. 27, 2004

(65) Prior Publication Data

US 2006/0025302 A1    Feb. 2, 2006

(51) Int. Cl.
*B01J 23/58* (2006.01)
*B01J 23/00* (2006.01)
*B01J 21/00* (2006.01)
*B01J 20/00* (2006.01)

(52) U.S. Cl. .............. 502/330; 502/304; 502/327; 502/328; 502/329; 502/347; 502/348; 502/349; 502/350; 502/332; 502/333; 502/339; 502/351; 502/355; 502/439

(58) Field of Classification Search ............ 502/304, 502/326, 327, 328, 329, 330, 332, 333, 339, 502/347, 348, 349, 350, 351, 355, 439
See application file for complete search history.

(56) References Cited

U.S. PATENT DOCUMENTS

| | | | |
|---|---|---|---|
| 2,359,759 A | 10/1944 | Hebbard et al. | |
| 2,802,889 A | 8/1957 | Frevel et al. | |
| 2,927,141 A | 3/1960 | Cohn e al. | |
| 3,651,167 A | 3/1972 | Rosset | |
| 3,726,936 A | 4/1973 | Pitzer | |
| 4,126,645 A | 11/1978 | Collins | |
| 4,329,530 A | 5/1982 | Irvine | |
| 4,390,456 A * | 6/1983 | Sanchez et al. ............ | 502/8 |
| 4,404,124 A | 9/1983 | Johnson et al. | |
| 4,409,410 A | 10/1983 | Cosyns et al. | |
| 4,484,015 A | 11/1984 | Johnson et al. | |
| 4,533,779 A * | 8/1985 | Boitiaux et al. ............ | 585/259 |
| 4,547,600 A | 10/1985 | Cosyns et al. | |
| 4,551,443 A * | 11/1985 | Hudson ...................... | 502/313 |
| 4,906,602 A * | 3/1990 | Schneider et al. .......... | 502/304 |
| 4,956,329 A * | 9/1990 | Chao et al. ................. | 502/251 |
| 5,059,732 A | 10/1991 | Cosyns et al. | |
| 5,266,548 A * | 11/1993 | Koradia et al. ............. | 502/439 |
| 5,364,998 A * | 11/1994 | Sarrazin et al. ............ | 585/259 |
| 5,475,173 A | 12/1995 | Cheung et al. | |
| 5,488,024 A | 1/1996 | Cheung et al. | |
| 5,489,565 A | 2/1996 | Cheung et al. | |
| 5,510,550 A | 4/1996 | Cheung et al. | |
| 5,587,348 A | 12/1996 | Brown et al. | |
| 5,648,576 A | 7/1997 | Nguyen Than et al. | |
| 5,739,075 A * | 4/1998 | Matusz ....................... | 502/302 |
| 5,889,187 A | 3/1999 | Than et al. | |
| 5,958,824 A * | 9/1999 | Rizkalla et al. ............. | 502/216 |
| 6,054,409 A | 4/2000 | Nguyen Thanh et al. | |
| 6,084,140 A * | 7/2000 | Kitamura et al. ........... | 585/260 |
| 6,184,175 B1 * | 2/2001 | Rizkalla ..................... | 502/347 |
| 6,204,218 B1 * | 3/2001 | Flick et al. ................. | 502/243 |
| 6,278,033 B1 | 8/2001 | Flick et al. | |
| 6,417,135 B1 * | 7/2002 | Dyroff ........................ | 502/325 |
| 6,509,292 B1 | 1/2003 | Blankenship | |
| 6,734,130 B2 | 5/2004 | Cheung et al. | |
| 6,797,669 B2 * | 9/2004 | Zhang et al. ................ | 502/339 |
| 6,987,080 B2 * | 1/2006 | Schmitz ...................... | 502/348 |
| 7,301,062 B2 * | 11/2007 | Gartside et al. ............ | 585/260 |
| 2002/0035033 A1 | 3/2002 | Muller et al. | |
| 2002/0165092 A1 | 11/2002 | Zhang et al. | |
| 2003/0171629 A1 * | 9/2003 | Ryu et al. ................... | 585/260 |
| 2004/0049061 A1 * | 3/2004 | Lockemeyer et al. ....... | 549/536 |

FOREIGN PATENT DOCUMENTS

| | | |
|---|---|---|
| CN | 1299858 | 6/2001 |
| EP | 839573 | 6/1998 |
| GB | 802100 | 10/1958 |
| GB | 1596959 | 9/1981 |
| WO | WO 2004/074220 | 9/2004 |

* cited by examiner

*Primary Examiner*—Cam N. Nguyen
(74) *Attorney, Agent, or Firm*—Scott R. Cox

(57) ABSTRACT

A catalyst for selective hydrogenation of acetylenes and diolefins, particularly in a raw gas feed stream for front end selective hydrogenation. The catalyst contains a low surface area carrier with a surface area from about 2-20 $m^2/g$, wherein the pore volume of the pores of the carrier is greater than about 0.4 cc/g, wherein at least 90 percent of the pore volume of the pores is contained within pores having a pore diameter greater than about 500 Å and wherein from about 1 to about 2 percent of the total pore volume is contained in pores with a pore diameter from about 500 to about 1,000 Å, palladium, wherein the palladium comprises from about 0.01 to about 0.1 weight percent of the catalyst, and a Group IB metal, wherein the Group IB metal comprises from about 0.005 to about 0.06 weight percent of the catalyst.

16 Claims, No Drawings

SELECTIVE HYDROGENATION CATALYST DESIGNED FOR RAW GAS FEED STREAMS

CROSS REFERENCE TO RELATED APPLICATIONS

NONE

BACKGROUND OF INVENTION

1. Field of Invention

This invention relates to selective hydrogenation catalysts, more particularly to improved, Group IB-promoted palladium catalysts with high pore volume and unique pore volume distribution. The catalysts are designed for the selective hydrogenation of butadiene, acetylenes, diolefins, and trace quantities of other such highly unsaturated hydrocarbon impurities in an olefinic feed stream, particularly in a raw gas feed stream containing $C_2$, $C_3$, $C_4$, $C_5$ and trace quantities of $C_6$ and higher hydrocarbons. This invention also relates to processes of preparation of these catalysts.

2. Prior Art

The manufacture of unsaturated hydrocarbons usually involves cracking various types of hydrocarbons. This process often produces a crude product containing hydrocarbon impurities that are more unsaturated than the desired product. This is particularly a problem with raw gas feed streams from cracking facilities containing $C_2$, $C_3$, $C_4$, $C_5$, and trace quantities of $C_6$ and higher hydrocarbons as well as hydrogen and methane. These raw gas feeds can contain significant unsaturated hydrocarbon impurities, such as 1,3 butadiene, methyl acetylene, propadiene, acetylene, isoprene, and trace quantities of other such unsaturated hydrocarbon impurities.

These unsaturated hydrocarbon impurities are often very difficult to remove completely by fractionation from a hydrocarbon feed stream. Further, it is often difficult, industrially, to hydrogenate these highly unsaturated hydrocarbon impurities without significant hydrogenation of the desired unsaturated hydrocarbons also occurring.

Two general types of gas phase selective hydrogenation processes for removing undesired, highly unsaturated hydrocarbons are commonly used: "front-end" hydrogenation and "tail-end" hydrogenation. "Front-end" hydrogenation involves passing the crude gas from the initial cracking step, often after removal of steam and condensable organic material, over a hydrogenation catalyst. The crude gas generally includes a relatively large volume of hydrogen and a mixture of unsaturated hydrocarbons. Among these products in raw gas feed streams may be $C_2$, $C_3$, $C_4$ and $C_5$ and trace quantities of $C_6$ and higher hydrocarbons and may be wet or dry. Typically, the hydrogen gas concentration is greater than the stoichiometric amount needed for complete hydrogenation of the impurities that are present in the crude gas. To minimize the risk of the excess hydrogen gas hydrogenating ethylene in the feed stream, the hydrogenation catalyst must be very selective. In addition, the catalyst risks being damaged in front-end reactions because hydrogenation of ethylene can lead to thermal excursion, known as "run-away", whereby high temperatures are experienced. Run-away can also result in severe loss of ethylene.

In "tail-end" hydrogenation, the crude gas is fractionated prior to hydrogenation resulting in concentrated product streams. Hydrogen is then added to these product streams, if necessary, such that a slight excess of hydrogen is present over the quantity required for complete hydrogenation of the impurities. In tail-end systems there is a greater tendency for deactivation of the catalyst, and consequently, periodic regeneration of the catalyst is necessary. While the quantity of hydrogen added can be adjusted to maintain selectivity, formation of polymers is a major problem in this process.

One catalyst that is preferred for selective hydrogenation reactions contains palladium supported on a low surface area carrier, such as a low surface area alumina. However, one of the problems with supported palladium catalysts is that under normal operating conditions not only are the impurities hydrogenated, but a substantial portion of the ethylene is also converted to ethane. In addition, these palladium on alumina catalysts often have relatively low stability over extended periods of time due to the formation of large quantities of oligomers on the catalyst surface. The rate of oligimerization is especially high when butadiene is present in the feedstream mixture. Further these palladium catalysts may not perform at acceptable levels when methyl acetylene, butadiene, isoprene, and other highly unsaturated compounds are present. For these reasons, these heavier compounds are normally removed by distillation prior to contact of the feed mixture with the catalyst.

Enhancers are often added to the palladium to improve the catalyst's properties. Copper, silver, gold, germanium, tin, lead, rhenium, gallium, indium, and thallium have been proposed as enhancers or modifiers for such palladium hydrogenation catalysts.

Acetylene hydrogenation catalysts for ethylene purification comprising palladium with a silver additive on a low surface area support material are disclosed in U.S. Pat. Nos. 4,404,124, 4,409,410, 4,484,015, 5,488,024, 5,489,565, 5,648,576, 6,054,409 and CN 1299858. Specifically, U.S. Pat. No. 6,054,409 discloses a catalyst for selective gas phase hydrogenation of acetylenic compounds containing two or three carbon atoms to the corresponding ethylenic compounds. The catalyst comprises palladium, at least one metal from group IB, optionally at least one alkali or alkaline-earth metal and alumina, in which at least 80% of the palladium and at least 80% of the element from group IB are present at the periphery of the catalyst, and wherein the IB metal/palladium ratio is 0.4 to 3 by weight.

In addition, U.S. Patent application 2002/0165092 discloses a catalyst for selective hydrogenation comprising palladium and a group IB metal promoter on an inorganic oxide support, wherein the active components are uniformly distributed between the surface and a depth of more than 300 microns. The catalyst is particularly applicable for feed streams containing $C_2$-$C_3$ fractions, hydrogen and CO.

In addition, U.S. Pat. No. 5,648,576 discloses a selective hydrogenation catalyst for acetylene compounds comprising from about 0.01 to 0.5 weight percent of palladium and from about 0.001 to 0.02 percent by weight of silver. Eighty percent (80%) or more of the silver is placed within a thin layer near the surface of the carrier body.

Catalysts containing palladium and Group IB metals (Cu, Ag, Au) on alumina used for the hydrogenation of acetylenes and diolefins have also been suggested by G.B. 802,100 and U.S. Pat. No. 2,802,889.

Selective hydrogenation catalysts of the prior art comprising palladium with a silver additive often do not exhibit the necessary selectivity and frequently cause significant loss of valuable olefins from the feed stream. This loss is especially a problem with prior art selective hydrogenation catalysts used in raw gas feed streams comprising hydrogen, methane, carbon monoxide and $C_4$, $C_5$, $C_6$ and higher hydrocarbons, which may be wet or dry.

Accordingly, it is an object of this invention to disclose a catalyst useful for selective hydrogenation of a $C_2$, $C_3$, $C_4$, $C_5$, $C_6$ and higher olefinic feed stream containing various acetylenic and diolefinic impurities.

It is a still further object of the invention to disclose a selective hydrogenation catalyst containing palladium supported on an inorganic support with a Group IB additive having a high pore volume and a unique pore volume distribution.

These and other objects can be obtained by the selective hydrogenation catalyst and the process for the preparation of the selective hydrogenation catalyst for use in olefinic feed stream containing acetylenic and diolefinic impurities, particularly raw gas feed streams and particularly for front end selective hydrogenation reactions, which are disclosed by the present invention.

SUMMARY OF THE INVENTION

The present invention is a catalyst for the selective hydrogenation of various highly unsaturated hydrocarbon impurities contained in an olefin-containing hydrocarbon feed. The catalyst comprises from about 0.01 to about 0.1 weight percent palladium and from about 0.005 to about 0.6 weight percent Group IB metal, preferably silver, wherein the ratio of the Group IB metal:palladium is from about 0.5:1 to about 6:1, incorporated into an inorganic support, wherein the surface area of the support is from about 2-20 m/g, wherein the pore volume of the support is greater than about 0.4 cc/g, wherein at least about 90%, preferably at least about 95% of the pore volume is contained in pores with pore diameters larger than about 500 Å, and wherein the pore volume of the pores with a pore diameter from about 500 to about 1,000 Å comprise from about 1 to about 2% of the total pore volume.

The present invention is also a process for the production of a catalyst for the selective hydrogenation of acetylenic and diolfinic impurities in a feed stream containing these impurities comprising preparing a carrier material in a suitable shape, wherein the surface area of the carrier material is from about 2 to about 20 $m^2/g$, wherein the pore volume of the carrier is at least about 0.4 cc/g, wherein at least about 90% of the pore volume is contained in pores with pore diameters larger than about 500 Å, and wherein the pore volume of pores with pore diameters from about 500 to about 1,000 Å is from about 1 to about 2% of the total pore volume and impregnating the carrier with a palladium compound, wherein the quantity of the palladium compound present in the catalyst after reduction comprises from about 0.01 to about 0.1 weight percent. Preferably at least about 90 percent of the palladium is located within about 250 microns of the surface of the catalyst. The process further comprises impregnating the palladium impregnated carrier with a Group IB metal additive, preferably silver, wherein the amount of the Group IB metal additive present in the catalyst, after reduction, comprises from about 0.005 to about 0.6 weight percent of the catalyst, wherein the ratio of the Group IB metal to the palladium is from about 0.5:1 to about 6:1.

The invention further comprises a process for the selective hydrogenation of acetylenic and diolefinic impurities, preferably in a raw gas feed stream without separation of individual components, preferably at low temperatures, comprising passing a raw gas feed stream, which contains acetylenic and diolefinic impurities, over the catalysts described above.

DETAILED DESCRIPTION

The invention is a catalyst for the selective hydrogenation of various impurities, such as acetylenes and diolefins, present in an olefin-containing hydrocarbon raw gas feed.

The invention further comprises a process for the production of catalysts that are useful for the selective hydrogenation of these impurities, such as acetylenes and diolefins, which are contained in a feed stream, preferably a raw gas feed stream.

The catalyst carrier may be any low surface area catalyst carrier, such as alumina, silica-alumina, zinc oxide, nickel spinel, titania, zirconia, ceria, chromia-alumina, magnesium oxide, cerium oxide and mixtures thereof. The preferred carrier is a low surface area alumina carrier. To qualify as a "low surface area" carrier, the carrier has a surface area less than about 20 $m^2/g$, preferably from about 2 to about 20 $m^2/g$, more preferably from about 2 to about 10 $m^2/g$, and most preferably from 3-5 $m^2/g$, as measured using the nitrogen method of determining surface area. The pore volume of the carrier is preferably greater than about 0.4 cc/g, more preferably greater than about 0.45 cc/g, and most preferably greater than about 0.5 cc/g. In addition, the carrier is selected such that at least about 90%, preferably at least about 95%, and most preferably at least about 98% of the pore volume is contained in pores with pore diameters greater than about 500 Å, wherein the pore volume of pores with pore diameters from about 500 to about 1,000 Å is from about 1 to about 2% of the total pore volume. It is important that carrier which is selected contain this specific pore volume and pore volume distribution to produce catalysts with enhanced performance, particularly enhanced selectivity and minimal loss of desired hydrocarbons, especially for selective hydrogenation reactions.

The catalyst carrier can be formed in any suitable shape, such as a sphere, cylinder, trilob, tablet and the like. In one preferred embodiment the catalyst carrier is formed as a sphere. The catalyst carrier can also be formed in any suitable size, preferably a sphere with a diameter from about 1 to about 5 mm, and more preferably from 1-3 mm.

The palladium can be introduced into the catalyst carrier by any conventional procedure which produces the proper palladium loading. One preferred technique involves impregnating the catalyst carrier with an aqueous solution of a palladium compound, such as palladium chloride. Preferably, the depth of penetration of the palladium compound into the carrier is controlled so that at least about 90 percent of the palladium compound is contained within about 250 microns of the surface of the catalyst carrier. Any suitable method can be used to control the depth of palladium penetration, such as is disclosed in U.S. Pat. Nos. 4,484,015 and 4,404,124, which patents are incorporated herein by reference.

After palladium impregnation, the impregnated material is calcined at a temperature from about 100° C. to about 600° C., preferably for about three hours. The palladium compound contained in the palladium catalyst precursor is then reduced, preferably by wet reducing, using a suitable wet reducing medium such as sodium formate, formic acid, hydrazine, alkali metal borohydrides, formaldehyde, ascorbic acid, dextrose and other conventional wet reducing agents.

Once the precursor catalyst material has been reduced, it is washed with deionized water to remove any halides, such as chlorides, to a level of less than about 100 ppm. The reduced catalyst composition is then dried at about 100° C. to 600° C. for a sufficient period of time.

The palladium impregnated precursor catalyst is then further impregnated with one or more Group IB metal compounds, such as Ag, Cu and Au, as an additive or additives. These compounds are preferably selected from silver salts, gold salts and/or copper salts or mixtures thereof. Preferably, the metal additive is silver impregnated in the form of a silver salt. The Group IB additive can be impregnated in the palladium impregnated precursor catalyst by any conventional process, such as by soaking or spraying the palladium impregnated precursor catalyst with an aqueous solution of the Group IB metal compound. For example, if the Group IB metal is silver, in one preferred embodiment the aqueous solution is a silver nitrate solution. After impregnation, the palladium impregnated catalyst material with the Group IB metal additive is then calcined at a temperature from about 100 to about 600° C. for about three hours. TheS catalyst is then reduced, preferably by heat treating with hydrogen for about 1 hour at about 80-120° C.

The amount of palladium present on the catalyst is from about 0.01 to about 0.1 weight percent, preferably 0.01 to 0.05 weight percent and most preferably from about 0.01 to about 0.03 weight percent, based on the total weight of the catalyst. The amount of the Group IB metal additive, preferably silver, that may be added is from about 0.005 to about 0.6 weight percent, preferably 0.01 to about 0.3 weight percent, and most preferably from about 0.01 to about 0.12 weight percent based on the total weight of the catalyst. The ratio of the Group IB additive present on the catalyst to the palladium is from about 0.5:1 to about 6:1, preferably about 1:1 to about 6:1 and most preferably from about 1:1 to about 4:1.

Following final drying, the palladium catalyst with Group IB metal additive is ready for use in a selective hydrogenation reactor, for example for the selective hydrogenation of impurities, such as butadiene, acetylenes and diolefins, particularly in a raw gas feed stream, without separation of individual components.

The palladium catalyst with a Group IB additive of the invention is designed primarily for the selective hydrogenation of impurities, such as acetylenes and diolefins, in admixture with other hydrocarbons, $H_2$ and CO, particularly in a raw gas feed stream. When the process is front end selective hydrogenation of a raw gas feed stream, the feed stream without separation normally includes substantial quantities of hydrogen, methane, $C_2$, $C_3$, $C_4$, $C_5$ and trace quantities of higher hydrocarbons, small quantities of carbon monoxide and carbon dioxide, as well as various impurities, such as 1,3 butadiene, acetylenes and diolefins, and may be wet or dry. The goal of the selective hydrogenation reaction is to reduce substantially the amount of the impurities present in the feed stream without substantially reducing the amount of desired hydrocarbons that are present.

In use, the palladium catalyst with Group IB metal additive is placed in a reactor. The inlet temperature of the feed stream in the reactor is raised to a level sufficient to hydrogenate the acetylene. Any suitable reaction pressure can be used. Generally, the total pressure is in the range of about 600 to 6750 kPa with the gas hourly space velocity (GHSV) in the range of about 1000 to about 14000 liters per liter of catalyst per hour.

The catalyst of the invention can be used for gas phase, liquid phase or combination gas and liquid phase applications. Regeneration of the catalyst may be accomplished by heating the catalyst in air at a temperature, preferably not in excess of 500° C., to burn off any organic material, polymers or char.

The subject catalyst exhibits improved hydrogenation of impurities, such as methyl acetylene, butadiene, and isoprene, in comparison to prior art catalysts. The presence of these higher acetylenes and diolefins improves the recovery of ethylene. The improved performance characteristics may not be obvious from the performance testing in the absence of impurities, such as methyl acetylene, propadiene, butadiene, isoprene and the like.

EXAMPLES

Example 1 (Comparative)

A commercially available catalyst manufactured by Süd-Chemie Inc. under the product name of G-83C is obtained. Analysis shows that the catalyst contains 0.018 weight percent of palladium and 0.07 weight percent of silver on an alumina carrier. The carrier for the catalyst has a BET surface area of about 4.3 m$^2$/g. The carrier has a total pore volume of 0.295 cc/g and a pore volume distribution in Å as follows:

| Pore Volume in Å | Percentage |
| --- | --- |
| 35.6-100.0 | 0.00% |
| 100.0-300.0 | 0.10% |
| 300.0-500.0 | 0.07% |
| 500.0-1000.0 | 0.27% |
| 1000.0-1622715.6 | 99.56% |

Example 2

Specially selected alumina spheres with a BET surface area of about 3.5 m$^2$/g using the nitrogen method are selected as the carrier for the catalyst of the invention. The carrier material selected has a total pore volume of 0.519 cc/g and a pore volume distribution in Å as follows:

| Pore diameter in Å | Percentage |
| --- | --- |
| 35.6 to 100 | 0.00% |
| 100.0-300.0 | 0.10% |
| 300.0-500.0 | 0.27% |
| 500.0-1000.0 | 1.71% |
| Above 1000.0 | 97.93% |

Catalyst spheres are prepared by dipping 25 grams of the specially selected alumina carrier spheres in a palladium chloride solution of sufficient concentration to yield a palladium loading of 0.018 weight percent with a palladium depth of penetration controlled to wherein at least about 90 percent of the palladium is within about 250 microns of the surface of the spheres. After palladium impregnation, the catalyst is calcined at 250° C. for about 3 hours. The catalyst is then wet reduced in a 5 percent aqueous sodium formate solution heated to a temperature of about 170° F. (76° C.) for about one hour. The catalyst is then washed free of chlorides (less than 100 ppm) with deionized water at about 160° F. (71° C.). The catalyst is then dried at about 250° F. (121° C.) for about 18 hours. The palladium containing precursor catalyst is then impregnated with silver by dipping the catalyst spheres in a silver nitrate solution of sufficient concentration to yield a silver loading of 0.05 weight percent. The catalyst is then calcined at 454° C. for three hours.

Performance Testing, Part 1:

Table 1, which follows, provides a comparison of the performance of Comparative Example 1 with Example 2 of the invention. The Examples are compared by passing a feed stream comprising 1448 ppm $C_2H_2$, 79 ppm $C_2H_6$, 18.3% $H_2$, 295 ppm CO, 35% CH$_4$ and 45% C$_2$H$_4$ over the catalysts. The catalysts are evaluated in a bench scale laboratory, three-quarter inch i.d. reactor tube, with a laboratory prepared, simulated front-end feed stock.

For each catalyst, the inlet temperature is varied and the conversion and selectivity of the catalyst are recorded. See the following Table:

TABLE 1

|  | Comparative Example 1 | Example 2 |
|---|---|---|
| Temperature (° C.) | 45 | 45 |
| Conversion | 92.90% | 93.40% |
| Selectivity | 64.40% | 77.80% |
| Temperature (° C.) | 48 | 48 |
| Conversion | 97.30% | 98.60% |
| Selectivity | 25.30% | 40.80% |
| Temperature (° C.) | 51 | 51 |
| Conversion | 98.70% | 99.70% |
| Selectivity | −27.00% | −10.10% |

In the above-referenced comparison, the catalyst activity is evaluated over a temperature range from 45° C. to 51° C. The percentage represents the percentage of acetylene that is converted into ethylene. As the reactor inlet temperature increases, the hydrogenation reaction becomes more active with a greater amount of C$_2$H$_2$ being hydrogenated and hence, removed from the product stream. However, some hydrogenation of C$_2$H$_4$ also occurs indicating a loss of selectivity for the reaction. "Selectivity" of each catalyst is reported as a percentage and is determined by the following calculation: 100 times ((inlet C$_2$H$_2$–outlet C$_2$H$_2$) minus (C$_2$H$_6$ outlet minus C$_2$H$_6$ inlet))/(C$_2$H$_2$ inlet minus C$_2$H$_2$ outlet). Higher positive percentages indicate a more selective catalyst. Data is obtained at a moderate GHSV (7000).

Comparisons of the conversion and the selectivity for the prior art catalyst of Comparative Example 1 to the inventive catalyst of Example 2 demonstrate the enhanced performance of the catalysts of the invention. Selectivity is significantly improved relative to the prior art catalysts. Further, the catalysts of the invention demonstrate a broader and lower temperature range over which the catalysts are active for hydrogenation than prior art catalysts.

The principles, preferred embodiments, and modes of operation of the present invention have been described in the foregoing specification. The invention, which is intended to be protected herein, however, is not to be construed or limited to the particular terms of disclosure, as these are to be regarded as being illustrative, rather than restrictive. Variations and changes may be made by those skilled in the art without departing from the scope of the invention.

The invention claimed is:

1. A catalyst for selective hydrogenation of acetylene comprising:
    a carrier having a low surface area with a surface area from about 2 to 20 m$^2$/g,
    palladium; and
    a Group IB metal,
    wherein the pore volume of the carrier is greater than about 0.4 cc/g, wherein at least about 90 percent of the pore volume of the pores is contained in pores with pore diameters greater than about 500 Å, and wherein from about 1 to about 2 percent of the pore volume is contained in pores with a pore diameter from about 500 to about 1,000 Å.

2. The catalyst of claim 1 wherein the palladium comprises from about 0.01 to about 0.1 weight percent of the catalyst, and wherein the Group IB metal comprises from about 0.005 to about 0.6 weight percent of the catalyst, and wherein the ratio of the Group IB metal to the palladium is from about 0.5:1 to about 6:1.

3. The catalyst of claim 1 wherein the Group IB metal is silver.

4. The catalyst of claim 1 wherein the depth of penetration of the palladium into the carrier is such that at least about 90 percent of the palladium is located within about 250 microns of the surface of the catalyst material, wherein the weight percentages are based on the total weight of the catalyst.

5. The catalyst of claim 1 wherein the composition of the carrier is selected from the group consisting of alumina, silica-alumina, zinc oxide, nickel spinel, titania, zirconia, ceria, chromia-alumina, magnesia, and mixtures thereof.

6. The catalyst of claim 1 wherein the carrier comprises alumina.

7. The catalyst of claim 1 which is formed in a shape selected from the group consisting of a sphere, trihole, monolith, pellet and tablet.

8. The catalyst of claim 7 wherein the shape of the catalyst is spherical and having a diameter from about 1 millimeter to about 5 millimeters.

9. The catalyst of claim 1 wherein the concentration of the palladium in the catalyst is from about 0.01 to about 0.05 weight percent based on the total weight of the catalyst.

10. The catalyst of claim 1 wherein the surface area of the carrier is from about 2 m$^2$/g to about 10 m$^2$/g.

11. The catalyst of claim 1 wherein the concentration of Group IB metal is from about 0.01 to about 0.3 weight percent based on the total weight of the catalyst.

12. The catalyst of claim 11 wherein the palladium comprises from about 0.01 to about 0.03 weight percent of the catalyst, and wherein the silver comprises from about 0.01 to about 0.12 weight percent, wherein the ratio of the silver to the palladium is from about 1:1 to about 4:1.

13. A catalyst for the selective hydrogenation of acetylene comprising:
    a carrier having a low surface area with a surface area from about 3-5 m$^2$/g,
    palladium, and
    silver,
    wherein the pore volume of the carrier is greater than about 0.5 cc/g, wherein at least about 98% of pore volume of the pores is contained in pores having a diameter greater than 500 Å, and wherein from about 1 to about 2% of the pore volume is contained in pores having a pore diameter from about 500 to about 1,000 Å.

14. The catalyst of claim 13 wherein at least about 90 percent of the palladium additive is located within about 250 microns of the surface of the catalyst.

15. The catalyst of claim 13 which is formed in a shape selected from the group consisting of a sphere, trihole, monolith, pellet and tablet.

16. The catalyst of claim 15 wherein the shape of the catalyst is spherical having a diameter from about 1 to about 3 millimeters.

* * * * *